(12) United States Patent
Rothfuss et al.

(10) Patent No.: US 10,124,493 B2
(45) Date of Patent: Nov. 13, 2018

(54) END EFFECTOR FOR AN INSTRUMENT

(71) Applicant: gomtec GmbH, Seefeld (DE)

(72) Inventors: Patrick Rothfuss, Hallbergmoos (DE); Bernd Gombert, Wörthsee (DE)

(73) Assignee: ABB GOMTEC GMBH, Seefeld (DE)

( * ) Notice: Subject to any disclaimer, the term of this patent is extended or adjusted under 35 U.S.C. 154(b) by 356 days.

(21) Appl. No.: 14/751,614

(22) Filed: Jun. 26, 2015

(65) Prior Publication Data

US 2016/0001448 A1 Jan. 7, 2016

(30) Foreign Application Priority Data

Jul. 4, 2014 (DE) .................. 10 2014 009 893

(51) Int. Cl.
*A61B 34/30* (2016.01)
*B25J 15/00* (2006.01)
*B25J 15/02* (2006.01)
*A61B 17/00* (2006.01)

(52) U.S. Cl.
CPC .......... *B25J 15/0028* (2013.01); *A61B 34/30* (2016.02); *B25J 15/028* (2013.01); *A61B 2017/00477* (2013.01); *A61B 2017/00876* (2013.01); *A61B 2034/305* (2016.02); *Y10S 901/31* (2013.01)

(58) Field of Classification Search
CPC ............ A61B 17/29; A61B 2017/2936; A61B 2017/2929; A61B 2017/2908; A61B 2017/2902; A61B 18/1445
See application file for complete search history.

(56) References Cited

U.S. PATENT DOCUMENTS

| 7,316,681 | B2 | 1/2008 | Madhani et al. | |
|---|---|---|---|---|
| 9,510,846 | B2* | 12/2016 | Sholev | A61B 17/068 |
| 2009/0326325 | A1* | 12/2009 | Naito | A61B 1/0055 600/141 |
| 2010/0010512 | A1* | 1/2010 | Taylor | A61B 17/04 606/144 |
| 2010/0331857 | A1* | 12/2010 | Doyle | A61B 34/30 606/130 |
| 2011/0087236 | A1* | 4/2011 | Stokes | A61B 17/29 606/130 |
| 2011/0276057 | A1* | 11/2011 | Conlon | A61B 17/29 606/130 |
| 2013/0190753 | A1* | 7/2013 | Garrison | A61B 17/29 606/41 |
| 2014/0165756 | A1* | 6/2014 | Aranyi | F16H 35/008 74/396 |
| 2014/0188159 | A1* | 7/2014 | Steege | A61B 17/29 606/207 |
| 2014/0221986 | A1* | 8/2014 | Kappel | A61B 17/29 606/1 |

FOREIGN PATENT DOCUMENTS

| AT | 507563 | 6/2010 |
|---|---|---|
| DE | 19813781 | 10/1999 |
| DE | 102012007645 | 10/2013 |
| WO | WO 9611636 | 4/1995 |

* cited by examiner

Primary Examiner — Julie A Szpira

(57) ABSTRACT

An end effector (60) comprises a base (63), a first gripper (64) connected with the base (63) so as to swivel around a gripper axis (68), and a positioning element (66) which is guided on the base displaceably along an end effector axis (76) and interacts with the gripper (64) via a guide slot system. The gripper axis (68) extends outside of a guide slot (70) of the guide slot system.

12 Claims, 9 Drawing Sheets

|  | Wheel | | | | Shaft (sleeve) | | |
| --- | --- | --- | --- | --- | --- | --- | --- |
|  | 31 | 32 | 33 | 34 | 41 | 42 | 44 |
| Actuation of grippers 64, 65 | X |  |  |  | R |  |  |
| Swivelling of end effector 60 |  |  | X |  | A | A |  |
| Rotation of end effector 60 | X | X | X |  | R | R |  |
| Rotation of swivel mechanism 79 |  |  |  | X |  |  | R |
Fig. 10
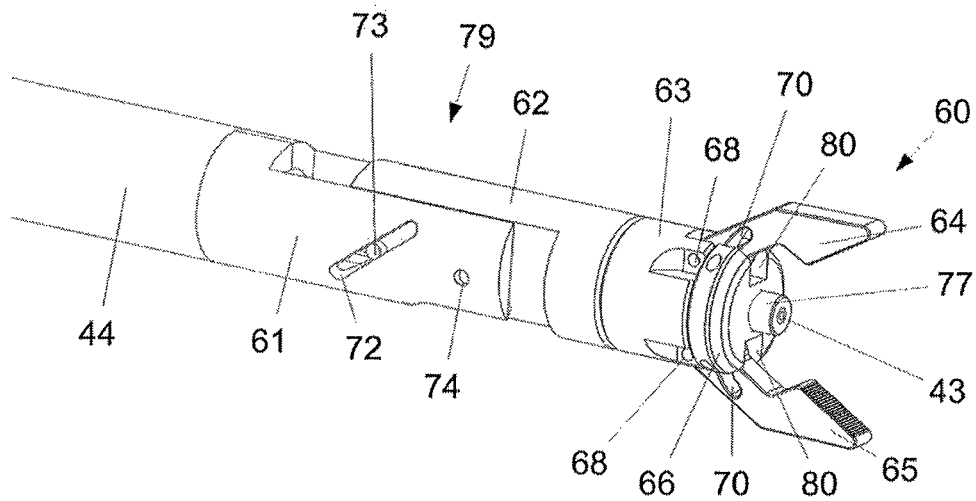
Fig. 11
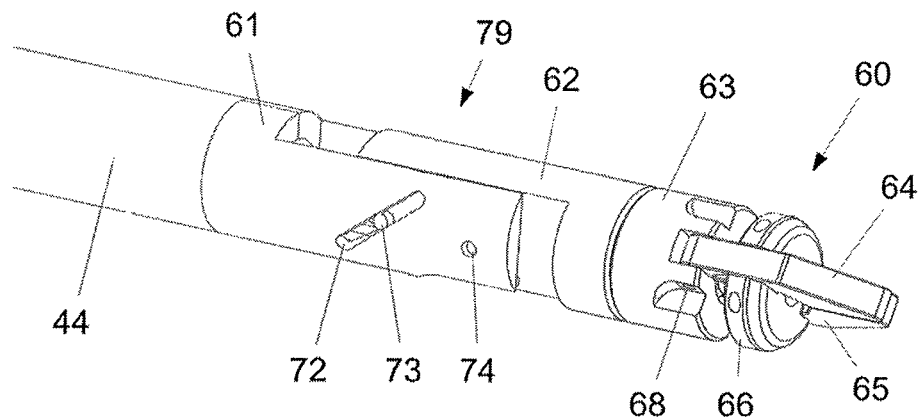
Fig. 12

END EFFECTOR FOR AN INSTRUMENT

The invention relates to an end effector for an instrument, preferably for an instrument wielded by a robot.

The publication U.S. Pat. No. 7,316,681 discloses a surgical instrument used in connection with a surgical robot in order to perform minimally invasive procedures. The instrument has a drive unit by means of which an end effector located on the end of the instrument shaft can be displaced. The actuating forces are transmitted from the drive unit to the end effector via several cables extending within the instrument shaft which are deflected via several pulleys located on the end effector.

Since, in order to perform the minimally invasive surgical procedures, it must be possible to introduce the end effector through small openings, the end effector together with the cable mechanism need to be of very finely detailed design. However, this finely detailed construction requires a high degree of precision in manufacture and is thus costly to produce. The cable mechanism also requires a specific pre-tensioning in order to be able to transmit the actuating forces from the drive unit to the end effector. If the pre-tensioning slackens over the course of time, this can have a negative influence on the correct functioning of the end effector.

The patent application WO96/11636 discloses an end effector designed as a gripping tool, the two grippers of which can be operated via a guide slot system. The grippers are mounted rotatably around a gripper axis. Each gripper has a guide slot which extends in a plane at right angles to the gripper axis, wherein the gripper axis passes through the guide slot. The grippers are actuated in that a bolt guided in the guide slots exerts an actuating force on the grippers, as a result of which the grippers are rotated around the gripper axis at a particular angle depending on the position of the bolt. The distance between bolt and gripper axis, together with the actuating force, determines the torque.

As the bolt passes along the guide slot it reaches a position in which the gripper axis extends through the bolt, i.e. the distance between bolt and gripper axis becomes zero. In this position, the bolt cannot apply any torque to the grippers, and the grippers are freely rotatable under the influence of an external torque. In particular, an object clamped between the grippers can no longer be held firmly when the bolt lies on the gripper axis, and there is a risk that the object may be lost. In addition, an uncontrolled rotation of the grippers can lead to the guide slots being oriented transversely to the direction of movement of the bolt, so that the bolt can no longer be displaced.

The invention is thus based on the problem of creating an instrument or an end effector which is distinguished through a robust construction and which dispenses with a cable mechanism with pulleys for the transmission of actuating forces. In addition, an end effector designed as a gripping tool with a guide slot system is to be proposed that is functionally reliable in all operating positions.

The object of the invention is achieved through an end effector comprising a base, a first gripper connected with the base so as to swivel around a gripper axis, a positioning element guided displaceably on the base along an end effector axis, which interacts with the gripper via a guide slot system, wherein the gripper axis extends outside of a guide slot of the guide slot system.

As a result of the spatial separation of gripper axis and guide slot it is possible to guarantee a transmission of force to the gripper in each operating position of the guide slot system. Depending on the operating position of the guide slot system, the gripper assumes a particular angle and maintains this angle in each operating position.

The further apart the guide slot and the gripper axis are from one another, the greater the clamping force of the gripper which can be achieved with a particular actuating force. For an appropriate transmission of force, the distance between guide slot and gripper axis at each point on the guide slot amounts to, advantageously, at least one third of the length of the guide slot.

In order to keep the size of a gripper comparatively small, the guide slot preferably extends between a plane perpendicular to the end effector axis, in which plane the gripper axis extends, and a clamping zone of the gripper. The clamping zone is located at the tip of the gripper and defines the region in which a gripper grips an object.

Alternatively, the guide slot could extend on the opposite side of the plane perpendicular to the end effector axis. However, in this case the gripper would have to be extended accordingly beyond the perpendicular plane in order for the gripper to be able to interact with the guide slot system.

The guide slot can be provided in the positioning element, and the bolt guided in the guide slot can be firmly connected with the gripper. Since the gripper rotates around the gripper axis, the bolt would rotate around the gripper axis at a constant distance from same.

Preferably however, the distance between gripper axis and bolt is variable. For this purpose the guide slot is recessed in the gripper, and a bolt of the positioning element can slide within the guide slot. The further the bolt is distanced from the gripper axis, the greater the clamping force of the gripper which can be achieved with a particular actuating force. As the gripper is closed, the positioning element together with the bolt should therefore move away from the gripper axis and the guide slot should be formed such that the gripper closes as the distance of the bolt from the gripper axis increases. The distance between an end of the guide slot facing the gripper axis and the end effector axis should therefore be chosen to be less than the distance between an end of the guide slot facing away from the gripper axis and the end effector axis. Preferably, the guide slot is curved, with the concave side facing the end effector axis.

The positioning element can have a cut-out through which the gripper extends, and the bolt is held in the positioning element on both sides of said cut-out. This cut-out offers the gripper, at least in the closed state, a lateral contact surface against which the gripper can be supported. This prevents the gripper from bending to the side when holding a heavy load and prevents the bolt from slipping out of the guide slot.

In a preferred embodiment, the positioning element has an inner thread which engages with an outer thread of a rotatable drive element. The inner and outer thread function as a worm gear which translates a rotary movement of a drive element into an axial longitudinal movement of the positioning element. For this purpose, the drive element can be mounted, rotatably and immovably in the axial direction, on the base of the end effector.

When closing, the gripper, which can swivel around the gripper axis, can press against a stationary gripper on the base of the end effector in order to grasp and hold an object between the two grippers. Alternatively, the end effector can have a second gripper which is connected with the base so as to swivel around a gripper axis. The second gripper is actuating analogously to the first gripper and interacts with the positioning element via a guide slot system.

The grippers can either swivel around a common gripper axis or each gripper can swivel around a gripper axis of its own. The separate gripper axes can in particular be tangents of a circle centred around the end effector axis.

In addition to the second gripper, the end effector can be equipped with further grippers, for example a third or fourth gripper.

The end effector can be connected with an elongated shaft sleeve of an instrument via a swivel mechanism. This allows the end effector to be swivelled in relation to the shaft sleeve. The swivelling movement is preferably controlled by means of a longitudinally displaceable shaft guided within the shaft sleeve.

The swivel mechanism can have a proximal member fixed to the shaft sleeve and a distal member connected with the end effector and the first shaft. The proximal and distal members can swivel relative to each other, preferably around a virtual swivel axis extending outside of the swivel mechanism.

The shaft guided within the shaft sleeve is, at least in a partial region, locally flexible. The flexible region preferably extends through the swivel mechanism. The flexible region is preferably elastically deformable and has the property, starting from a curved position, of once again assuming an axially extended, uncurved position.

The proximal member and the distal member are preferably connected together by means of two axially spaced guide slot systems. One of the guide slot systems can comprise a guide slot on the distal member and a bolt on the proximal member and the other guide slot system can comprise a guide slot on the proximal member and a bolt on the distal member. If the shaft is axially displaced within the shaft sleeve, a force is transmitted to the distal member and moves the latter along the guide slots. Since the guide slots have a path which is not parallel with the longitudinal axis of the instrument, the longitudinal movement transmitted from the shaft to the distal member is deflected around the virtual swivel axis, causing the distal member to swivel.

The forces transmitted via the swivel mechanism act on the bolts guided in the guide slots. The further apart the bolts are spaced along the guide slots during a displacement of the distal member, the greater the leverage effect of the transmitted forces. In order to be able to withdraw the end effector from a spatially restricted working area at any time, the end effector must always be able to arrive safely at a configuration in which it is aligned in a straight line with the shaft. If the distance between the bolts is the greater the closer the swivel mechanism approaches a configuration in which it is extended in a straight line, then the torque by means of which the swivel mechanism can be brought back into this configuration in which it is aligned in a straight line is always greater than that available to bend the swivel mechanism, so that the straight-line configuration can always be safely achieved again.

The base of the end effector is preferably connected rotatably with the distal member of the swivel mechanism, so that the grippers can be rotated around the end effector axis. In this case the shaft guided within the shaft sleeve is firmly connected with the base of the end effector and housed rotatably within the shaft sleeve. The rotary movement of the base can then be controlled through rotation of the shaft. The end effector can thus be rotated and swivelled simultaneously through simultaneous rotation and longitudinal displacement of the shaft.

In an advantageous embodiment of the invention, the shaft guided within the shaft sleeve is also sleeve-formed in design, so that a second shaft can be guided within it. This second shaft accommodated within the first shaft can be connected with the positioning element of the end effector in order to make possible an actuation of the positioning element.

For example, the second shaft can be connected with the aforementioned drive element which is in threaded engagement with the positioning element and can drive it in a rotary direction.

Other features and advantages of the invention are explained in the following description of exemplary embodiments with reference to the attached figures, in which.

Figure 6:
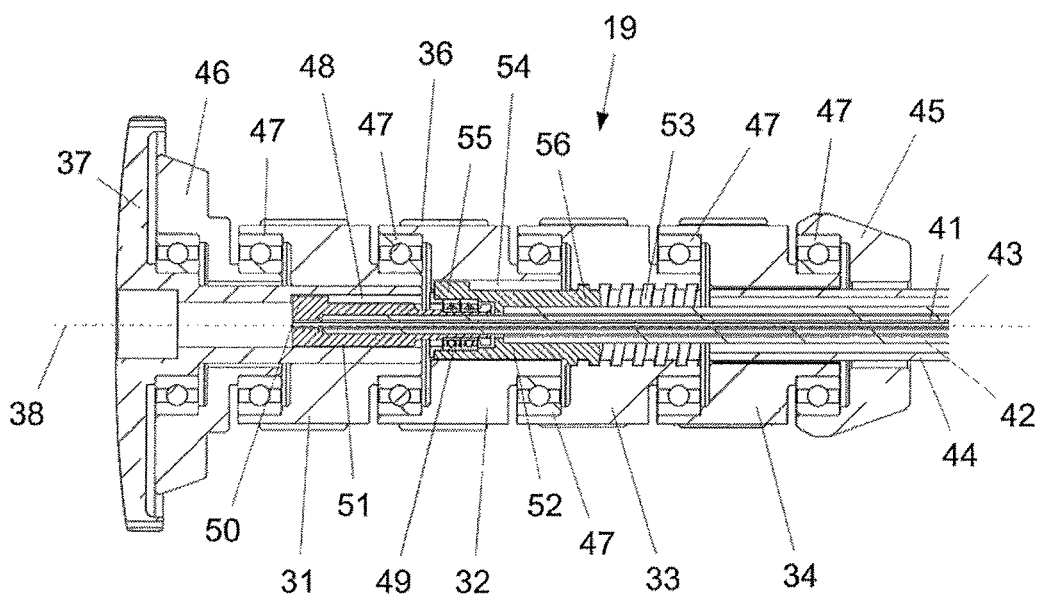
Figure 7:
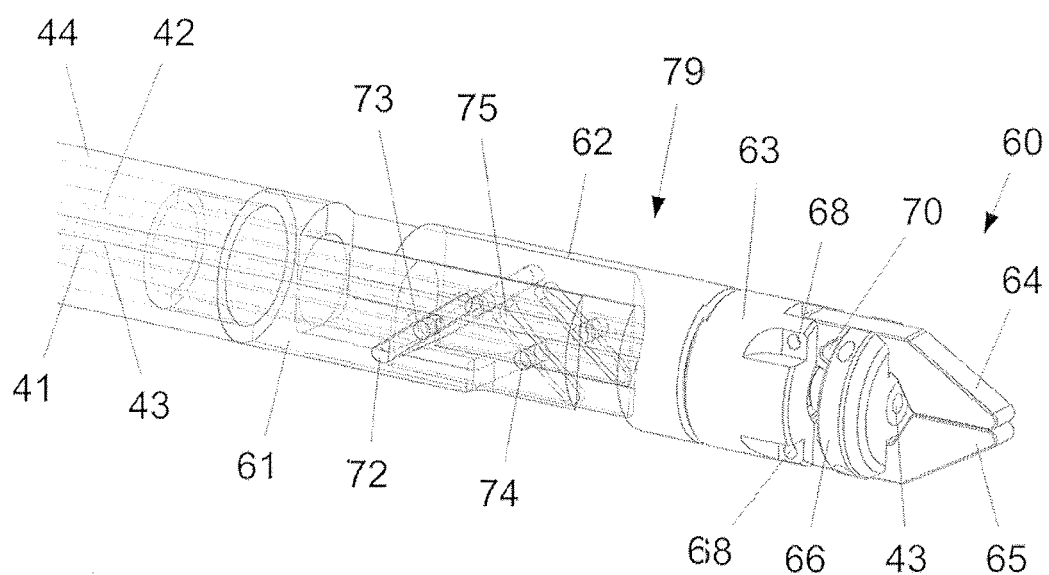
Figure 8:
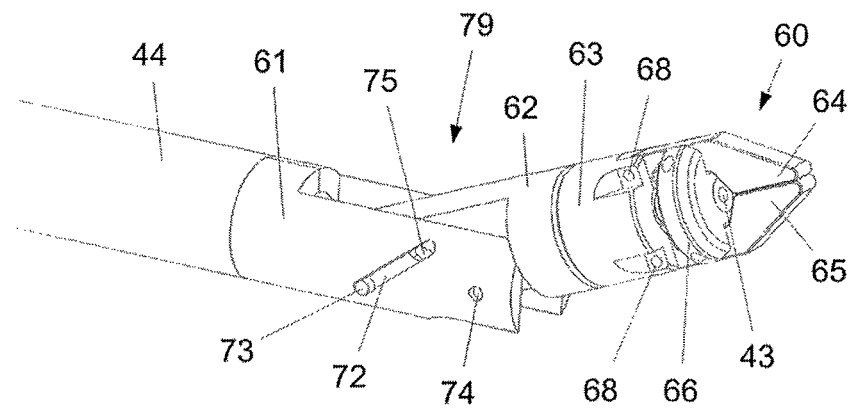
Figure 9:
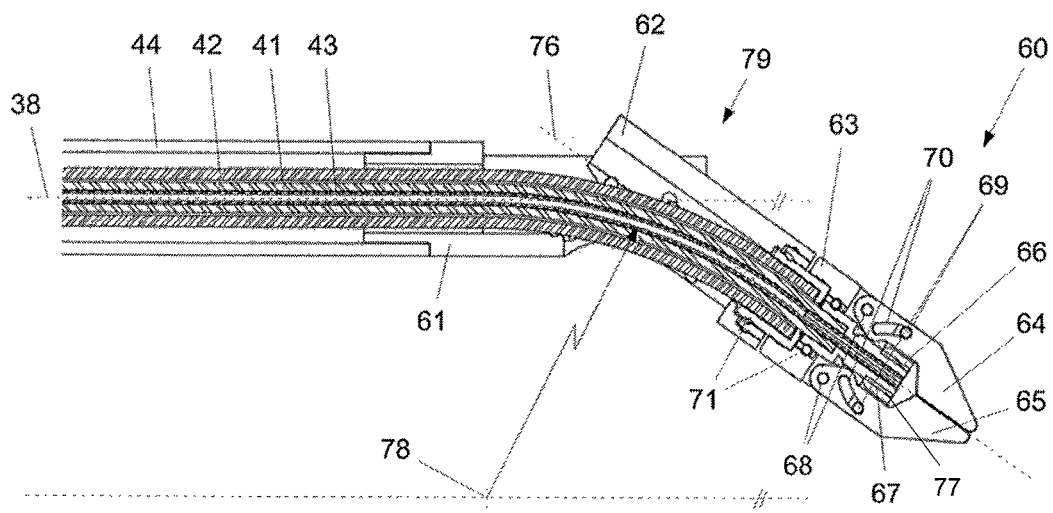
Figure 13:
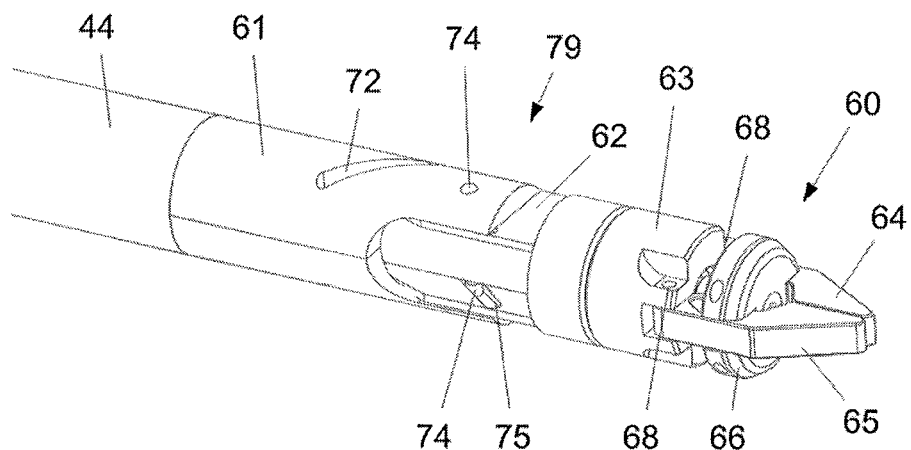
Figure 14:
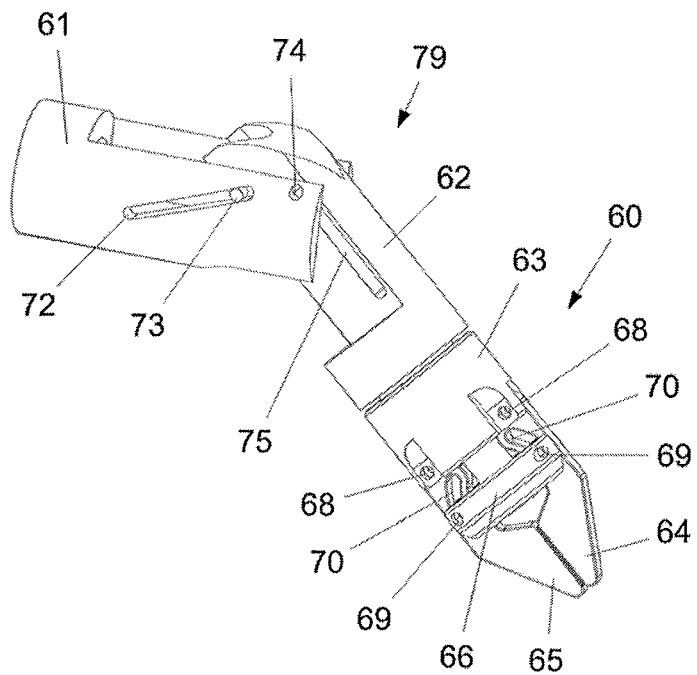
Figure 15:
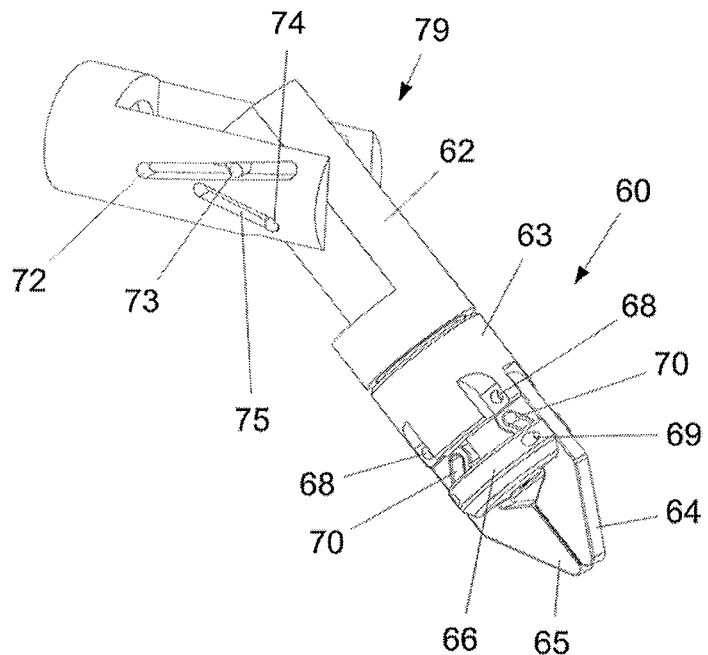
Figure 16:
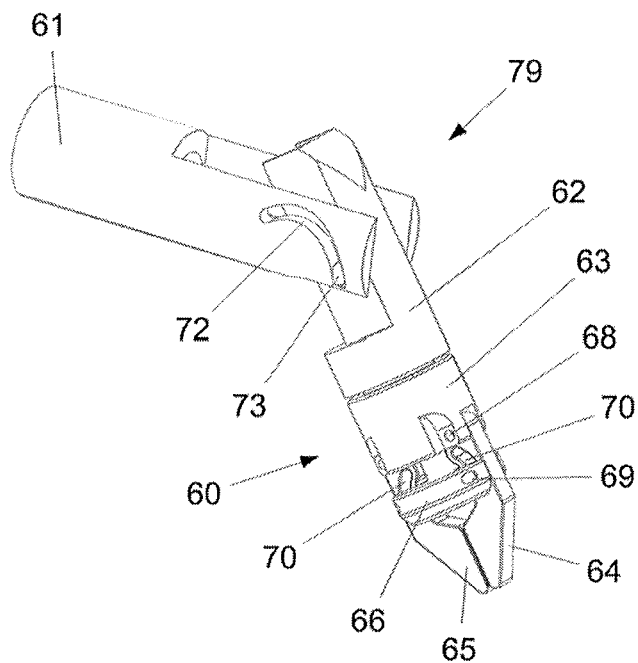

FIG. 6 shows a cross section of an actuation unit on the proximal end of the instrument, FIG. 7 shows a distal end of the instrument with a swivel mechanism and an end effector in extended position, FIG. 8 shows the distal end of the instrument shown in FIG. 7 in angled position, FIG. 9 shows a cross section of the distal end of the instrument, FIG. 10 shows an overview in table form of the possible ways of actuating the instrument;

FIG. 11 shows the distal end of the instrument with grippers of the end effector in opened position;

FIG. 12 shows the distal end of the instrument with the end effector rotated in relation to the swivel mechanism;

FIG. 13 shows the distal end rotated around the longitudinal axis of the instrument;

FIG. 14 shows a distal end with a second embodiment of the swivel mechanism;

FIG. 15 shows a distal end with a third embodiment of the swivel mechanism;

FIG. 16 shows a distal end with a fourth embodiment of the swivel mechanism.

Figure 1:
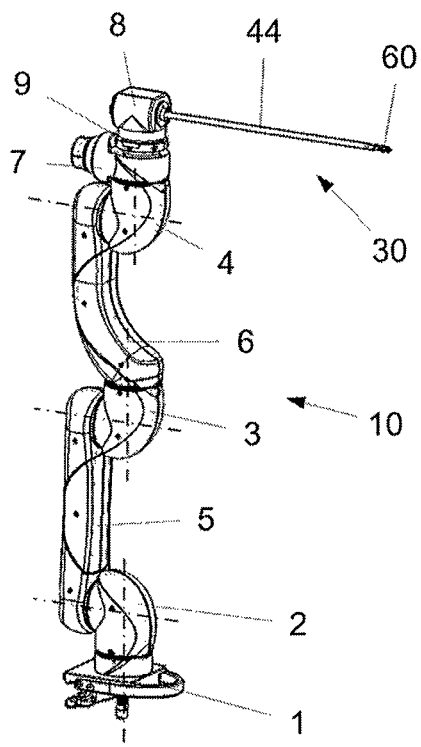
FIG. 1 shows a robot equipped with an instrument.

FIG. 1 shows a robot 10 and an instrument 30 coupled with the robot 10. The robot 10 comprises an attachment element 1, which serves to attach the robot 10 to any suitable object. The attachment element 1 connects with a joint 2 which rotatably connects an arm element 5 with the attachment element 1. A second arm element 6 is connected rotatably with the arm element 5 via a joint 3. Connected to the arm element 6 via a further joint 4 is an input device 7 which allows the user to control the robot 10 and/or the instrument 30.

Each of the three joints 2, 3 and 4 has two axes of rotation oriented at right angles to each other, so that a rotary movement is possible on two connection sides of a joint. The robot 10 can thus be moved in six degrees of freedom. In order to allow corresponding control of the robot 10 the input device 7 preferably has a cap which can also be moved manually in six degrees of freedom. A more detailed explanation of such a robot control system can be found in the applicant's as yet unpublished patent application DE102013019869.

A distal end of the robot 10 is formed by a drive unit 8 which is firmly connected with the input device 7 via a flange 9. The instrument 30 can be coupled, replaceably, with the drive unit 8 and driven or actuated via the drive unit 8.

Figure 2:
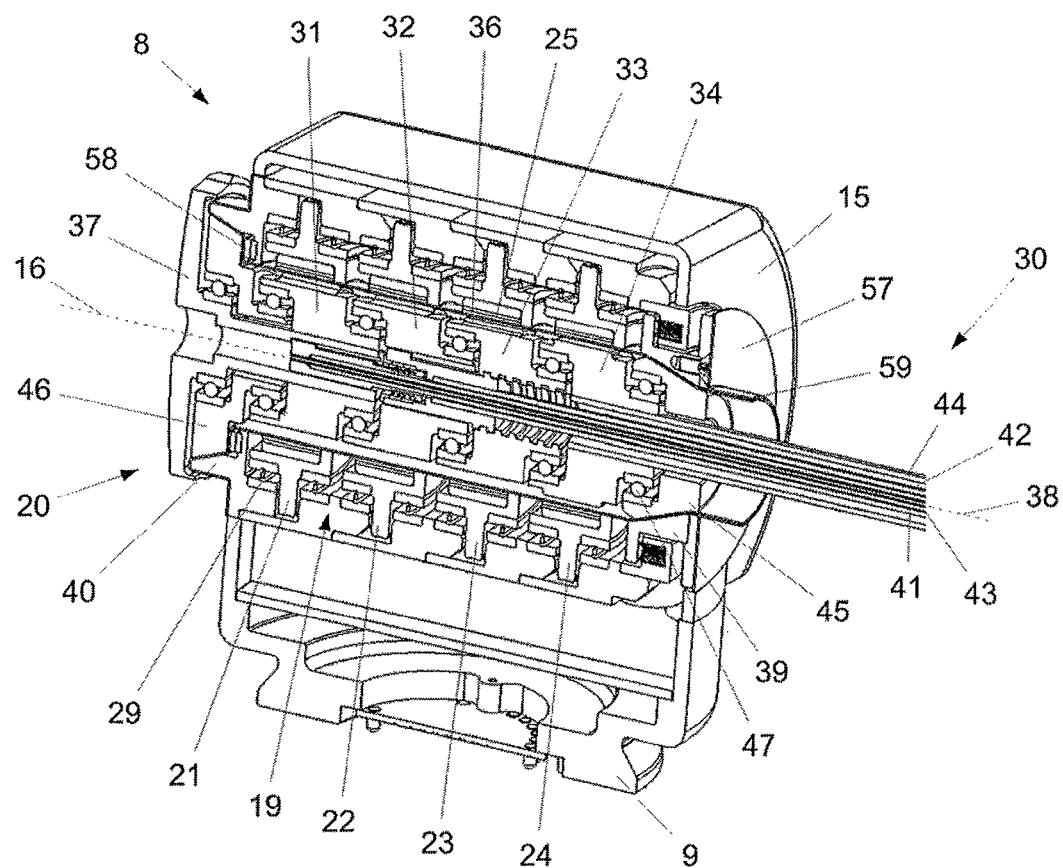
FIG. 2 shows a cross section through a drive unit with an inserted instrument.
Figure 3:
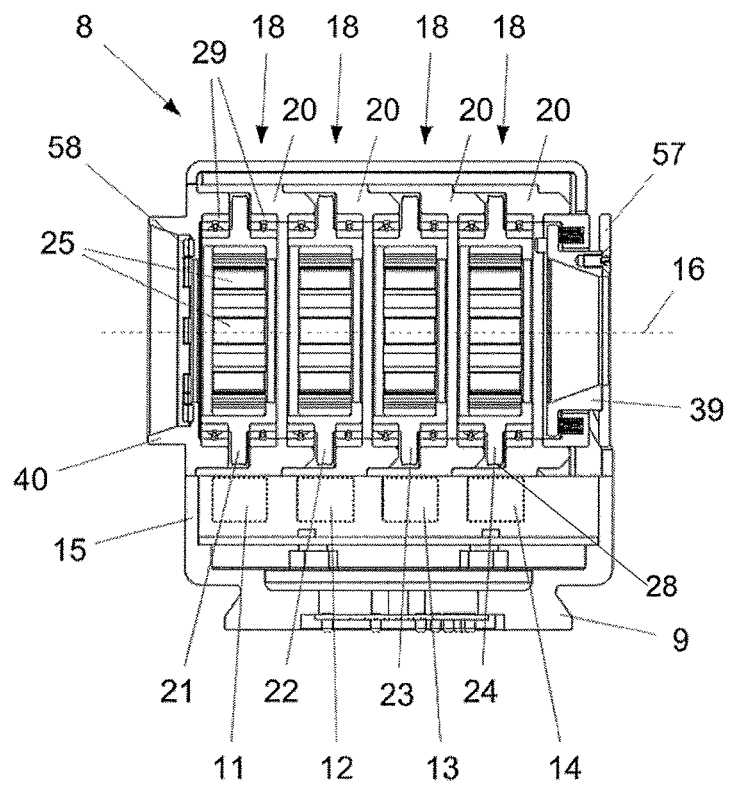
FIG. 3 shows a cross section through the drive unit without the instrument.
Figure 4:
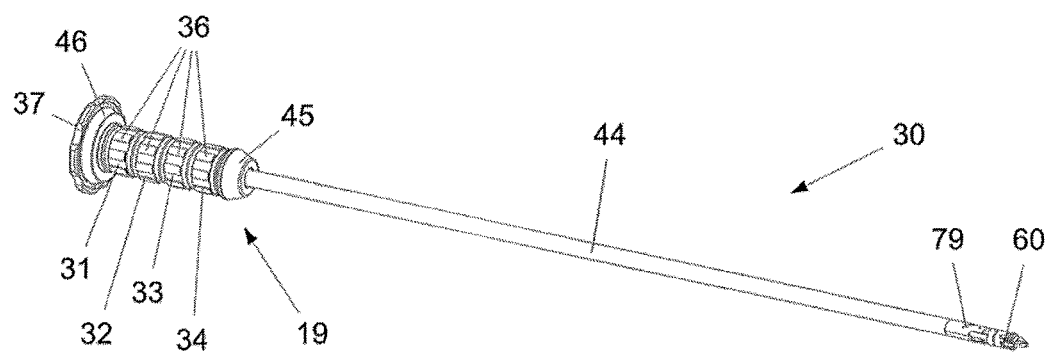
FIG. 4 shows the instrument.

FIG. 2 shows the drive unit 8 with the inserted instrument 30 in cross section, FIG. 3 shows the drive unit 8 without the instrument in cross section, and FIG. 4 shows the instrument 30 detached from the drive unit 8.

The instrument 30 possesses an actuation unit 19 with four wheels 31, 32, 33 and 34, a base element 46 adjacent, on the left, the left-hand outer wheel 31 and a support element 45 adjacent, on the right, the right-hand outer wheel 34. The wheels 31, 32, 33 and 34 are rotatable in relation to one another and in relation to the base and support elements 45, 46 in order to drive movements of an end effector 60 connected with a shaft sleeve 44 by means of a swivel mechanism 79. The base element 46 and the support element 45 are formed so as to taper conically in the direction of the end effector 60.

The drive unit 8 has a housing 15 which is firmly connected with the flange 9. The drive unit 8 is hollow throughout along an axis 16, so that the instrument 30 can be inserted into the drive unit 8 from one side along the axis 16 in order to couple the instrument 30 with the drive unit 8.

In the coupled state of the instrument 30, the support element 45 rests against a correspondingly formed stop 39 in the housing 15 of the drive unit 8. The stop 39 is mounted resiliently in the housing 15 and generates a pre-tensioning force on the instrument 30.

The side of the housing 15 opposite the stop 39 has a further stop 40 against which the base element 46 of the instrument 30 rests in the coupled state.

The stop 40 is also preferably conical in form, corresponding to the base element 46.

The stops 39 and 40 prevent the instrument 30 from slipping through in an axial direction. The conical design of the two stops 39 and 40 as well as of the support and base elements 45 and 46 of the instrument 30 creates a specifically defined plug-in position of the instrument 30 in an axial direction and in a radial direction with respect to the axis 16. As FIG. 2 shows, a coaxial alignment of a longitudinal axis 38 extending through the instrument 30 with the axis 16 extending through the drive unit 8 can thus be achieved.

A retaining element 58 is preferably provided on the housing 15 which fixes the instrument 30 detachably with the housing 15, in order, in the coupled state, to prevent a rotation of the base element 46 in relation to the housing 15 or an axial slippage within the drive unit 8 along the axis 16. The retaining element 58 can comprise a magnet which exerts a holding force on the base element 46, which is made of ferromagnetic material.

Four identical drive modules 18 are built into the drive unit 8. The first drive module comprises a magnetic ring 21 driven by a motor 11, the second drive module comprises a magnetic ring 22 driven by a motor 12, the third drive module comprises a magnetic ring 23 driven by a motor 13 and the fourth drive module comprises a magnetic ring 24 driven by a motor 14. The magnetic rings each comprise a hollow-cylindrical inner section fitted with magnets 25 and an outer section in the form of a gear rim 28 projecting radially from the inner section. All four magnetic rings 21, 22, 23 and 24 are mounted in the housing 15 with, in each case, at least one roller bearing 29, in this case with two roller bearings 29, one on each side of the outer section.

Figure 5:
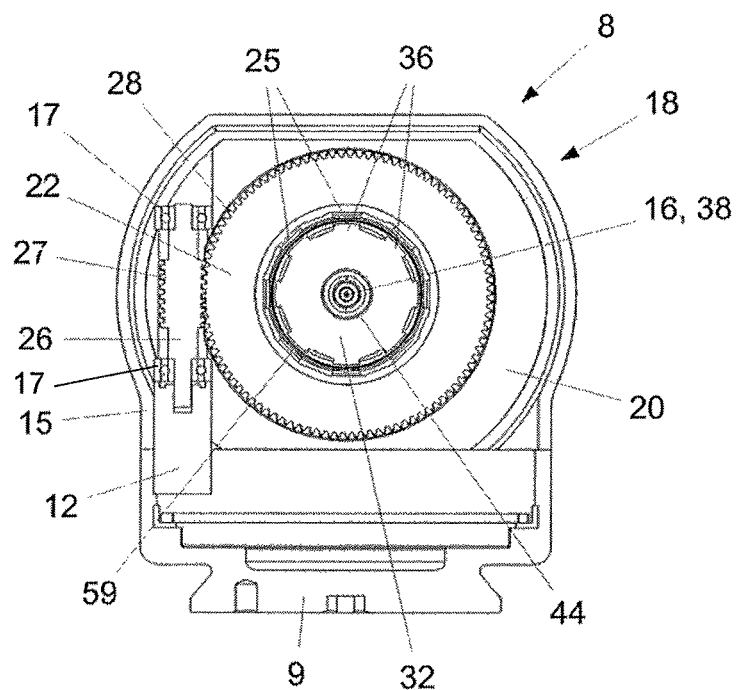
FIG. 5 shows a cross section through a drive module of the drive unit.

To represent all four drive modules 18, FIG. 5 shows their structure and functional principle with reference to the example of the second drive module 18. The drive module 18 has a stable mounting segment 20. The motor 12 is firmly connected with the mounting segment 20 and drives a gear 26.

The gear 26 is in this case designed as a worm gear and has a worm 27 which engages with the gear rim 28. The worm 27 is mounted rotatably in relation to the mounting segment 20 by means of bearings 17 and transmits the torque generated by the motor 12 to the magnetic ring 22 in order to drive it in a rotary manner around the axis 16. The magnetic ring 22 thus functions as a worm wheel and is connected with the motor 12 in a mechanically force-transmitting manner.

As can be seen in FIG. 3, the individual drive modules 18 are plug-connected together via their mounting segments 20, in that each mounting segment 20 has a projection on its right-hand side, as seen in FIG. 3, which engages into a complementary recess in the adjacent mounting segment 20 on the right, so that the gear rims 28 are flanked to the right and left by different mounting segments 20.

On the one hand, the plugged connection permits a modular structure and a fixed alignment of the mounting segments 20 in relation to one another. On the other hand, the mounting segments 20 serve the purpose of fixing to the housing 15 of the drive unit 8, with which they can for example be screwed or also plugged together.

The four drive modules 18 are arranged next to one another and aligned coaxially in relation to one another, so that each magnetic ring 21, 22, 23 and 24 can rotate around the common axis 16. Motors of the four drive modules 18 can be actuated individually, so that the magnetic rings 21, 22, 23 and 24 can be rotated independently of one another.

When a magnetic ring 21, 22, 23, 24 rotates, the magnets 25 fixed to the magnetic ring in question rotate with it. Permanent magnets are preferably used as magnets 25. Alternatively, electromagnets can also be used.

Each of the four wheels 31, 32, 33, 34 of the actuation unit 19 of the instrument 30 is arranged concentrically to the longitudinal axis 38 of the instrument 30 and is surrounded by a magnetic ring 21, 22, 23 or 24 when the instrument 30 is coupled with the drive unit 8, i.e. the magnetic ring 21 is arranged concentrically around the wheel 31, the magnetic ring 22 is arranged concentrically around the wheel 32 and so on. (see FIGS. 2 and 4).

Each wheel 31, 32, 33, 34 has on its periphery a driving-force-transmitting structure in the form of several ferromagnetic bodies 36 which form a magnetic positive connection with the magnets 25. The motor-driven magnetic rings 21, 22, 23 and 24 therefore serve on the one hand to couple the instrument 30 detachably with the drive unit 8 and on the other hand to transmit torques to a wheel 31, 32, 33 and 34 of the actuation unit 19 of the instrument 30 corresponding to the respective magnetic ring 21, 22, 23 and 24, i.e. each magnetic ring 21, 22, 23, 24 is in magnetic force-transmitting connection with a corresponding wheel 31, 32, 33, 34.

FIG. 6 shows the actuation unit 19 of the instrument 30 in cross section. Every two of the four wheels 31, 32, 33, 34 are connected with one another via a roller bearing 47, so as to rotate around the longitudinal axis 38, and are arranged next to one another at a fixed distance. The left-hand outer wheel 31 is rotatably supported on the base element 46 by a bearing 47 pressed onto the base element 46. The right-hand outer wheel 34 is supported on the support element 45 by a bearing 47 pressed into the support element 45.

In the bearings 47 arranged between two wheels 31, 32, 33, 34, an outer ring of the bearing 47 is pressed into one of the wheels 31, 32, 33, 34 and an inner ring of the bearing 47 is pressed onto the other wheel 31, 32, 33, 34.

The bearings 47 arranged on each side of the wheels 31, 32, 33, 34 ensure the axial integrity of the construction elements connected by the bearings 47.

As shown in FIG. 6, the ferromagnetic bodies 36 can overlap the bearings 47 in an axial direction in order to make optimal use of the surface area available on the periphery of a wheel.

The wheel 32 adjacent the left-hand wheel 31 is connected, non-rotatably, with a first shaft 42. The non-rotatable connection is in the form of a tongue-groove connection with a tongue 55 connected with the first shaft 42 and a groove 54 formed in the wheel 32 and makes possible an axial relative movement as well as a transmission of a torque between the first shaft 42 and the wheel 32. The tongue 55 can, as in this case, be part of a right-hand sleeve 52 with which the first shaft 42 is firmly connected. Instead of the tongue-groove connection, a splined shaft connection, for example, could also be selected.

The first shaft 42 engages in an inner thread 53 of the wheel 33 adjacent the right-hand wheel 34 by means of an outer thread 56. The outer thread 56 is located on the sleeve 52 firmly connected with the first shaft 42.

The outer thread 56 and the inner thread 53 form a screw thread which converts a rotary movement of the second wheel 33 into a translatory movement of the first shaft 42 along the longitudinal axis 38. The pitch of the thread determines the transmission ratio and thus the advance per rotation.

The difference in the lengths of the groove 54 and tongue 55 determines the axial freedom of movement of the first shaft 42. Alternatively, other rotary-translatory conversion gears can be selected, for example a ball screw drive.

The two wheels 32, 33 interact such that, when one of the two wheels 32, 33 rotates, the first shaft 42 performs a translatory or axial movement along the longitudinal axis 38, and when both wheels 32, 33 rotate simultaneously it performs a rotary movement around the longitudinal axis 38.

The wheel 34 is firmly connected with the shaft sleeve 44, which is arranged coaxially with the first shaft 42 and surrounds it. Through rotation of the third wheel 34, the shaft sleeve 44 is driven and rotates relative to the first shaft 42 around the longitudinal axis 38. The end effector 60, connected with the shaft sleeve 44 by means of the swivel mechanism 79, is also rotated around the longitudinal axis 38.

A second shaft 41 is arranged, coaxially with the longitudinal axis 38, within the first shaft 42, which in this case is hollow throughout. The second shaft 41 is connected with the first shaft 42, rotatably but in an axially fixed manner, by means of (roller) bearings 49; i.e. a relative movement between the first and second shafts 41, 42 is only possible through a rotary movement, but not through an axial movement. The second shaft 41 can thus rotate relative to the first shaft 42 around the common longitudinal axis 38 and in the event of an axial movement of the first shaft 42, it is carried along by the latter, so that the second shaft 41 always moves together with the first shaft 42 in an axial direction, but can rotate independently of the latter.

The second shaft 41 is connected non-rotatably with the wheel 31. The non-rotatable connection is in the form of a tongue and groove connection, a tongue 50 being connected with the second shaft 41 and a groove 48 being formed in the wheel 31, and makes possible an axial relative movement of the second shaft 41 and the wheel 31 as well as a transmission of a torque between them. Where, in the event of an axial movement of the first shaft 42, the second shaft 41 is carried along by the latter, the second shaft 41 can move freely in the wheel 31 in an axial direction.

The tongue 50 can, in this case, be part of a left-hand sleeve 51 with which the second shaft 41 is firmly connected. Instead of the tongue-groove connection, a splined shaft connection, for example, could also be selected. The difference in the lengths of the groove 48 and tongue 50 determines the axial freedom of movement of the second shaft 41. Since the first and second shafts move together in an axial direction, the difference in the lengths of the groove 48 and tongue 50 is the same as the difference in the lengths of the groove 54 and tongue 55.

The end effector 60 located on the distal end of the instrument 30 is swivelably connected with the shaft sleeve 44 via a swivel mechanism 79. The swivel mechanism 79 comprises a proximal member 61, which is firmly connected with the shaft sleeve 44. In a further development of the invention, the proximal member 61 and the shaft sleeve 44 can be formed as a single piece.

A distal member 62 of the swivel mechanism 79, which is coupled onto a base 63 of the end effector 60, is swivelably connected to the proximal member 61.

The swivelable connection of the proximal and distal members 61 and 62 can comprise any form of swivel bearing in which the proximal member 61 serves as a thrust bearing of the distal member 62. As FIG. 7 (with concealed edges) and FIG. 8 (without concealed edges) show, in this exemplary embodiment a guide slot system is chosen as swivel bearing, in which a guide slot 72 is formed in the proximal member 61 and a guide slot 75 is formed in the distal member 62.

A guide slot 72, 75 of the member 61, 62 interacts with a bolt 73, 74 fixed to the other member 62, 61, in that the course of the guide slot 72, 75 serves as a guide for the bolt 73, 74. At least one of the guide slots 72, 75 has a course which is not parallel with the longitudinal axis 38 of the instrument 30. The course is preferably linear, but can, alternatively, also be curved.

In the event of a relative movement of the distal member 62 the bolts 73, 74 guided in the guide slots 72, 75 follow the course of the guide slots and cause the distal member 62 to swivel accordingly, whereby an end effector axis 76 extending longitudinally through the end effector 60 is oriented at an angle in relation to the longitudinal axis 38 of the instrument 30. As shown in FIG. 9, the swivelling movement takes place around a swivel axis 78 which runs normally to the longitudinal axis 38. The end effector 60 coupled onto the distal member 62 swivels with it, accordingly.

The end effector 60 can swivel in the direction shown in FIG. 9 or in a direction opposite thereto (as shown in FIG. 8). The swivelling movement in one direction or in the opposite direction is in each case performed around a swivel axis which extends normally to a parallel of the longitudinal axis 38. In FIG. 9 the end effector 60 swivels around the swivel axis 78, in FIG. 8 it swivels around a swivel axis (not shown) located at a distance from and running parallel to the swivel axis 78.

In an alternative embodiment of the invention, the swivel mechanism can be realised with only a single guide slot system in which a guide slot is recessed either into the proximal member or into the distal member and in each case interacts with a bolt of the other member and the bolt has a cross section, elongated in the direction of the guide slot, which engages, non-rotatably, in the guide slot.

The first shaft 42 and the second shaft 41 have at least one flexible partial region. This partial region extends through the swivel mechanism 79 and makes it possible for the first shaft 42 and the second shaft 41 to follow a swivelling movement of the distal member 62, swivelling accordingly.

The flexible partial region of the two shafts 41, 42 is preferably elastically deformable.

As FIG. 9 shows, the distal end of the first shaft 42 is firmly connected with the base 63 of the end effector 60. Thus, the base 63 of the end effector 60 can be moved by means of the first shaft 42. If the first shaft 42 is driven in a rotary movement, then the base 63 is rotated relative to the swivel mechanism 79 around the end effector axis 76.

If the first shaft 42 is driven in an axial direction, then the base 63 of the end effector 60 is also moved in an axial direction, whereby the distal member 62 of the swivel mechanism 79 connected with the base 63 is at the same time displaced along the guide slot 72 or 75 and performs a swivelling movement around the swivel axis 78, i.e. the end effector 60 can be swivelled through an axial movement of the first shaft 42.

If the shaft sleeve 44 is driven in a rotary movement, the swivel mechanism 79 rotates together with the end effector 60 around the longitudinal axis 38.

The end effector is designed according to the intended purpose of the instrument 30 (e.g. industrial or surgical application) and comprises for example a camera, a light source, a blade, a welding electrode or any other type of tool. In this exemplary embodiment, the end effector 60 is designed as a gripping tool and has two grippers 64 and 65, each of which is connected with the base 63 so as to be rotatable around a gripper axis 68.

The base 63 is connected with the distal member 62 of the swivel mechanism 79 so as to be rotatable, by means of bearings 71, around the end effector axis 76 extending through the distal member 62 and the base 63.

Each of the grippers 64 and 65 is connected with a positioning element 66. The connection is in the form of a guide slot system in which, preferably, each gripper 64 and 65 has a guide slot 70 and the positioning element 66 has a corresponding bolt 69. Alternatively, the reverse arrangement could be chosen.

The positioning element 66 is mounted so as to be axially displaceable along the end effector axis 76. The movement of the positioning element 66 is driven through the second shaft 41. For this purpose, a drive element 77 is attached at the distal end of the shaft 41 which engages with the positioning element 66 by means of screw threads 67. The screw thread 67 translates a rotary movement of the second shaft 41 into an axial movement of the positioning element 66 along the end effector axis 76.

Through a displacement of the positioning element 66, the bolts 69 are displaced along the end effector axis 76 and slide along the path defined by the guide slots 70. The bolts 69 thereby press laterally against the guide slots 70, so that, depending on the direction of movement of the positioning element 66, the grippers 64 and 65 are spread or closed together. Advantageously, the guide slots 70 are formed such that the grippers 64 and 65 are pressed together when the positioning element 66 is moved away from the base 63 and such that the grippers 64 and 65 are spread when the positioning element 66 is moved towards the base 63 in order that the forces acting from the bolt 69 onto the grippers 64, 65 are translated into the greatest possible clamping forces when the grippers 64, 65 are closed.

The guide slot 70 of each gripper 64, 65 and its gripper axis 68 are arranged such that the gripper axis 68 extends outside of the guide slot 70 of the guide slot system. This prevents the bolt 69 guided in the guide slot 70 of the gripper 64, 65 from being able to assume a position which coincides with the gripper axis 68 of the gripper 64, 65, i.e. the gripper axis 68 and bolt 69 are always spaced apart, so that the force acting on the bolt 69 always generates a torque around the gripper axis 68.

As shown in FIG. 9, the guide slot 70 can be located next to a plane, perpendicular to the end effector axis 76, in which the gripper axes 68 of the grippers 64, 65 extend, without intersecting this plane. In this exemplary embodiment, the guide slots 70 extend between this plane and a clamping zone or the tip of their respective gripper 64, 65, in order to make the best use of the available construction space in the grippers 64, 65.

In order for the greatest possible torque to be applied at the grippers 64, 65 as they close, in the closed state of the grippers 64, 65 the bolts 69 must assume a position in the guide slots 70 in which the distance between bolts 69 and gripper axis 68 of a gripper 64, 65 is at a maximum. For this purpose, the guide slots 70 of each gripper 64, 65 are designed such that the distance between an end of the guide slot 70 facing the gripper axis 68 and the end effector axis 76 is less than the distance between an end of the guide slot 70 facing away from the gripper axis 68 and the end effector axis 76. In this case the grippers 64, 65 are closed when the bolts 69 are moved away from the gripper axes 68 and towards the clamping zone of the grippers 64, 65.

In order to provide the end effector 60 with good stability, in addition to being compact, a cut-out 80 is provided in the positioning element 66 for each gripper 64, 65, as shown in FIG. 11. On the one hand, the bolts 69 are held in the positioning element 66 on both sides of their respective cut-out 80, so that the cut-outs 80 form an accommodation for the bolts 69. On the other hand, the grippers 64, 65 can, in the closed state, be supported against a lateral contact surface of the cut-out 80. This prevents the grippers 64, 65 from bending away to the side when holding a heavy load. In addition, this accommodation of the grippers 64, 65 prevents the bolts 68 from slipping out of their guide slots 70.

A continuous channel 43 can be integrated within the instrument 30 which can be used to convey media, for example to rinse the end effector 60 or the object which is to be gripped by the end effector 60 or to deliver gas. The channel 43 is preferably formed by a cavity in the second shaft 41, as shown in FIGS. 6 and 9.

The instrument 30 can also have on the proximal end a handle 37 connected non-rotatably with the second shaft 41 (see FIGS. 4 and 6). This handle 37 can be used to insert the instrument 30 into the drive unit 8 or remove it. Through manual rotation of the handle 37 the second shaft 41 can be actuated which—as explained above—controls the grippers. This allows the user to open the grippers 64, 65 manually via the drive unit 8 in the event of a malfunction of the motor drive.

FIG. 10 summarises the individual actuation possibilities in table form and once again illustrates the functional principle of the wheels 31, 32, 33 and 34, the shaft sleeve 44 and the shafts 41 and 42 as well as their effects on the actuation of the end effector 60. A distinction is made between the following forms of actuation: actuation of the grippers 64, 65 (see FIG. 11); swivelling of the end effector 60 around the swivel axis 78 (see FIGS. 8 and 9); rotation of the end effector 60 around the end effector axis 76 (see FIG. 12) and rotation of the swivel mechanism 79 together with the end effector 60 around the longitudinal axis 38 (see FIG. 13). The wheels which must be driven in order to perform the relevant actuation are marked with an "X". The movement of the shaft sleeve or the shafts effected by the driven wheels are marked "R" or "A", wherein "R" defines a rotary movement and "A" defines an axial movement.

Accordingly, the second shaft 41 is rotated through rotation of the fourth wheel 31 alone. The direction of rotation of the second shaft 41 determines whether the positioning element 66 is moved towards or away from the base 63 and, accordingly, causes the grippers 64 and 65 to open or close.

Through rotation of the second wheel 33, the first shaft 42 is shifted in an axial direction. The second shaft 41 is carried along by the first shaft 42 and is thus also shifted axially. The axial movement of the first shaft 42 causes a displacement of the base of the end effector 60 which is superimposed on a swivelling movement, around the swivel axis 78, of the distal member 62 of the swivel mechanism 79 connected with the base 63.

In order to rotate the end effector 60 in relation to the swivel mechanism 79, around the end effector axis 76, the first shaft 42 is caused to rotate through synchronous rotation of the first and second wheels 32 and 33. In order to prevent an adjusting movement of the positioning element 66, which would trigger an actuation of the grippers 64 and 65 caused through the difference in rotational speed between the first and second shaft 41, 42, the second shaft 41 is rotated synchronously with the first shaft 42 by driving the fourth wheel 31.

By driving of the third wheel 34, the shaft sleeve 44 and thus the swivel mechanism 79 connected with it is rotated around the longitudinal axis 38. In order also to rotate the end effector 60 together with the swivel mechanism 79, all the wheels 31 to 34 can be driven simultaneously, so that the two shafts 41 and 42 rotate together with the shaft sleeve 44.

FIGS. 14 to 16 show alternative embodiments of the swivel mechanism 79. In the embodiment shown in FIG. 7 the guide slot 72 of the proximal member 61 extends non-parallel or at an angle to the longitudinal axis 38 of the instrument 30 and the guide slot 75 of the distal member 62 extends non-parallel or at an angle to the end effector axis 76. In contrast, FIG. 14 shows a swivel mechanism 79, wherein one of the guide slots 72, 75 extends parallel to one of the axes 38, 76; in this case then, the guide slot 75 of the distal member 62 extends parallel to the end effector axis 76.

In contrast to FIG. 7, FIG. 15 shows a swivel mechanism 79, wherein the bolts 73 and 74 are arranged in one member 62 and the guide slots 72 and 75 are arranged on the other member 61. In this variant the two bolts 73 and 74 are thus always at the same distance from one another.

FIG. 16 shows a swivel mechanism 79 with only one guide slot 72 and only one bolt 73. Since in this case the bolt 73 is wider than in FIG. 7, it can be supported on its own, non-rotatably, against the guide slot 72, i.e. the second guide slot system for supporting the torque of the distal member 62 on the proximal member 61 can thus be dispensed with.

The invention claimed is:

1. An instrument (30) comprising:
   an end effector (60);
   an elongated shaft sleeve (44);
   a first shaft (42) guided within the elongated shaft sleeve (44), wherein the first shaft (42) is at least locally flexible and is guided so as to be longitudinally displaceable within the elongated shaft sleeve (44);
   a swivel mechanism (79) which connects the end effector (60) and the elongated shaft sleeve (44) and is driven by said first shaft (42), said swivel mechanism (79) having a proximal member (61) fixed to the elongated shaft sleeve (44) and a distal member (62) connected with the end effector (60) and the first shaft (42), which proximal and distal members (61, 62) are connected via two axially spaced guide slot systems and are configured so as to swivel relative to each other around a virtual swivel axis (78) extending outside of the swivel mechanism (79); and
   wherein a first one of the two axially spaced guide slot systems comprises a guide slot (75) on the distal member (62) and a bolt (74) on the proximal member (61), and a second one of the two axially spaced guide slot systems comprises a guide slot (72) on the proximal member (61) and a bolt (73) on the distal member (62);
   wherein said end effector (60) comprises a base (63), a first gripper (64) connected with the base (63) so as to swivel around a first gripper gripper axis (68), a positioning element (66) which is guided on the base displaceably along an end effector axis (76) and interacts with the gripper (64) via a guide slot system, wherein the positioning element (66) has an inner thread which engages with an outer thread of a rotatable drive element (77) and wherein the rotatable drive element (77) is mounted rotatably and immovably in the axial direction on the base (63), and wherein the gripper axis (68) extends outside of a guide slot (70) of a guide slot system.

2. The instrument according to claim 1, characterised in that a distance between the guide slot (70) and gripper axis (68) is equal to at least one third of a length of the guide slot (70).

3. The instrument according to claim 1, characterised in that the guide slot (70) extends between a plane perpendicular to an end effector axis (76) in which the gripper axis (68) extends, and a clamping zone of the gripper (64).

4. The instrument according to claim 1, characterised in that the guide slot (70) is recessed in the gripper (64) and a bolt (69) of the positioning element (66) is displaceable within the guide slot (70).

5. The instrument according to claim 4, characterised in that the distance between an end of the guide slot (70) facing the gripper axis (68) and an end effector axis (76) is less than the distance between an end of the guide slot (70) facing away from the gripper axis (68) and the end effector axis (76).

6. The instrument according to claim 5, characterised in that the guide slot (70) is curved, and wherein a concave side of said curved guide slot (70) facing the end effector axis (76).

7. The instrument according to claim 4, characterised in that the positioning element (66) has a cut-out (80) through which the gripper (64) extends, and the bolt (69) of the positioning element (66) is held in the positioning element (66) on both sides of the cut-out (80).

8. The instrument according to claim 1, characterised in that a second gripper (65) is connected with the base (63) so as to swivel around a second gripper gripper axis (68) and interact with the positioning element (66) via a guide slot system.

9. The instrument according to claim 8, characterised in that the first gripper gripper axis (68) and the second gripper gripper axis (68) are two tangents to a circle centred around the end effector axis (76).

10. The instrument (30) according to claim 1, characterised in that a distance between the bolt (74) on the proximal member (61) and the bolt (73) on the distal member (62) is the greater the closer the swivel mechanism (79) approaches a configuration in which it is extended in a straight line.

11. An instrument (30) comprising:
an end effector (60);
an elongated shaft sleeve (44);
a first shaft (42) guided within the elongated shaft sleeve (44), wherein the first shaft (42) is at least locally flexible and is guided so as to be longitudinally displaceable within the elongated shaft sleeve (44);
- a swivel mechanism (79) which connects the end effector (60) and the elongated shaft sleeve (44) and is driven by said first shaft (42), said swivel mechanism (79) having a proximal member (61) fixed to the elongated shaft sleeve (44) and a distal member (62) connected with the end effector (60) and the first shaft (42) and wherein the distal member (62) is connected rotatably and immovably in an axial direction with the base (63), and wherein the first shaft (42) is anchored non-rotatably on the base (63), which proximal and distal members (61, 62) are connected via two axially spaced guide slot systems and are configured so as to swivel relative to each other around a virtual swivel axis (78) extending outside of the swivel mechanism (79); and
wherein a first one of the two axially spaced guide slot systems comprises a guide slot (75) on the distal member (62) and a bolt (74) on the proximal member (61), and a second one of the two axially spaced guide slot systems comprises a guide slot (72) on the proximal member (61) and a bolt (73) on the distal member (62).

12. An instrument (30) comprising:
an end effector (60);
an elongated shaft sleeve (44);
a first shaft (42) guided within the elongated shaft sleeve (44), wherein the first shaft (42) is at least locally flexible and is guided so as to be longitudinally displaceable within the elongated shaft sleeve (44);
a second shaft (41), disposed within the first shaft (42), and coupled to a positioning element (66);
a swivel mechanism (79) which connects the end effector (60) and the elongated shaft sleeve (44) and is driven by said first shaft (42), said swivel mechanism (79) having a proximal member (61) fixed to the elongated shaft sleeve (44) and a distal member (62) connected with the end effector (60) and the first shaft (42), which proximal and distal members (61, 62) are connected via two axially spaced guide slot systems and are configured so as to swivel relative to each other around a virtual swivel axis (78) extending outside of the swivel mechanism (79); and
wherein a first one of the two axially spaced guide slot systems comprises a guide slot (75) on the distal member (62) and a bolt (74) on the proximal member (61), and a second one of the two axially spaced guide slot systems comprises a guide slot (72) on the proximal member (61) and a bolt (73) on the distal member (62).

* * * * *